US005470327A

United States Patent [19]

Helgren et al.

[11] Patent Number: 5,470,327

[45] Date of Patent: Nov. 28, 1995

[54] POINTED ADAPTER FOR BLUNT ENTRY DEVICE

[75] Inventors: R. Hayes Helgren, Mundelein; David E. Kramer, Northbrook, both of Ill.

[73] Assignee: Abbott Laboratories, Abbott Park, Ill.

[21] Appl. No.: 308,870

[22] Filed: Sep. 20, 1994

Related U.S. Application Data

[63] Continuation of Ser. No. 84,666, Jun. 29, 1993, abandoned.

[51] Int. Cl.[6] .......... A61M 37/00

[52] U.S. Cl. .......... 604/411; 604/88

[58] Field of Search .......... 604/87, 88, 239–240, 604/243–244, 272, 411–412, 414–415; 128/760, 763

[56] References Cited

U.S. PATENT DOCUMENTS

| | | | |
|---|---|---|---|
| 4,457,749 | 7/1984 | Bellotti et al. | 604/29 |
| 4,588,403 | 5/1986 | Weiss et al. | 604/411 |
| 4,614,437 | 9/1986 | Buehler | 366/130 |
| 4,675,020 | 6/1987 | McPhee | 604/411 |
| 4,759,756 | 7/1988 | Forman et al. | 604/413 |
| 4,936,841 | 6/1990 | Aoki et al. | 604/413 |
| 5,171,214 | 12/1992 | Kolber et al. | 604/82 |
| 5,342,346 | 8/1994 | Honda et al. | 604/413 |
| 5,356,380 | 10/1994 | Hoekwater et al. | 604/85 |
| 5,411,499 | 5/1995 | Dudar et al. | 604/411 |

FOREIGN PATENT DOCUMENTS

| | | |
|---|---|---|
| 351643 | 1/1990 | European Pat. Off. . |

*Primary Examiner*—Corrine M. Maglione
*Attorney, Agent, or Firm*—A. Nicholas Trausch

[57] ABSTRACT

The present invention relates to a pointed adapter which enables a blunt entry device such as a blunt cannula to readily penetrate an elastomeric closure such as a conventional vial stopper. The adapter also includes a collar which initially protects the adapter point from touch contamination and from accidental stick to the user.

11 Claims, 2 Drawing Sheets

POINTED ADAPTER FOR BLUNT ENTRY DEVICE

This application is a continuation of U.S. patent application Ser. No. 08/084,666, filed Jun. 29, 1993 now abandoned.

FIELD OF THE INVENTION

The present invention relates generally to a pointed adapter which enables a blunt entry device such as a blunt cannula to readily penetrate an elastomeric closure such as a conventional medical stopper. More particularly, the adapter includes a collar having a stem that mates with the blunt end of the cannula and initially protects the adapter point from touch contamination and from accidental stick to the user.

BACKGROUND OF THE INVENTION

Elastomeric closures are commonly used to seal various sterile medical containers currently in use, such as vials and flexible solution bags. For example, elastomeric stoppers are used to close small volume unit dose glass vials. Likewise elastomeric reseals are used to close the ports of flexible plastic containers such as IV solution bags.

The elastomeric closures described above permit access into the sealed container only by penetrating the elastomeric closure. Conventionally, the elastomeric closures have thick dimensions to withstand sterilization and shelf storage. The resiliency of the elastomer and the thick dimensions requires a sharp or pointed entry device such as a syringe needle or a piercing pin to penetrate the closures. The elastomeric closure reseals after the entry device is withdrawn, potentially permitting multiple entries.

The majority of medical stoppers and reseals currently in use are molded of medical grade elastomeric compounds in a thickness that does not allow easy penetration by any entry device other than a sharp or pointed device. Thus the material and configuration (i.e. thickness) of conventional elastomeric closures requires use of a sharp or pointed entry device to gain access to the sealed container.

With increasing concern about diseases such as HIV and AIDS, which are carried by bodily fluids, the use of "sharp" devices in the healthcare environment is being minimized. Sharps have the potential to breach the skin barrier by an "accidental stick" and thereby potentially transmit disease. It is estimated that more than one half of the sharps currently used in hospitals are used only for fluid transfer and connection involving IV administration sets. These sharp "connectors" can be replaced by blunt cannula and pre-pierced reseals such as the Lifeshield® Blunt Cannula and the Lifeshield® Prepierced Reseal, both sold by Abbott Laboratories.

However, when withdrawing a solution or drug from a vial with a sharp needle syringe, the user must exercise care. The majority of elastomeric closures for drug or solution vials currently in use cannot be readily pierced by a blunt entry devices such as the LifeShield® Blunt Cannula. Thus, sharp needles remain in use.

Recent concerns about drug effects due to accidental sticks has led to the desire to reduce the need for healthcare providers to use sharp needles for access to drug vials. Vial adapters have been introduced to shield the healthcare provider from the sharp cannula which penetrates the vial. The other end of the cannula may include a standard luer connector for fluid communication with a syringe barrel having a compatible luer connector. Alternatively, as disclosed in U.S. Pat. No. 5,100,394 to Dunbar, et al titled, "Pre-Slit Injection Site", the opposite end of the cannula may include a pre-slit septum compatible with a blunt cannula entry device. However, healthcare providers are reluctant to use the available vial adapters since the adapters increase the time for set-up and change-over, created additional waste material for disposal and added additional expense.

Thus, it is an object of the present invention to provide a pointed adapter that is compatible with blunt entry devices for fluid access through thick elastomeric closures such as vial stoppers.

It is another object of the present invention to provide an adapter which is economical to manufacture and easy to use.

It is another object of the present invention to provide an adapter which indicates previous use.

Another object of the present invention is to provide an adapter which does not require undue force by the health care provider to insert the blunt entry device, while still protecting the user from accidental stick and the adapter from touch contamination.

Other important objects of the present invention will become readily apparent from the following description and drawings.

SUMMARY OF THE INVENTION

The present invention relates to a pointed member adapted for use with a blunt cannula to pierce a medical closure such as an elastomeric stopper or reseal. The piercing member includes an annular collar having a rearward end adapted for an interference fit around the blunt end of the blunt cannula and a forward end adapted to abut the closure. A piercing element is concentrically positioned within the annular collar and has a pointed tip oriented forward within the forward end of the collar. A radially extending annular shoulder on the piercing element defines the rear end of the pointed tip. The shoulder is adapted to abut the exposed blunt end of the cannula. A base portion extends rearward from the shoulder within the rearward end of the collar. An integral and frangible connection radially connects the annular collar and the piercing element. The adapter further includes a base portion configured as a stem adapted to fit within the cannula bore. The piercing member is a conical tip. The frangible connection is a thin annular membrane between the conical tip and the rearward end of the collar.

Other features and advantages of the present invention will become readily apparent from the following detailed description, the accompanying drawings, and the appended claims.

DETAILED DESCRIPTIONS OF THE PREFERRED EMBODIMENTS

Figures 1, 2, 2A, 3, 4:
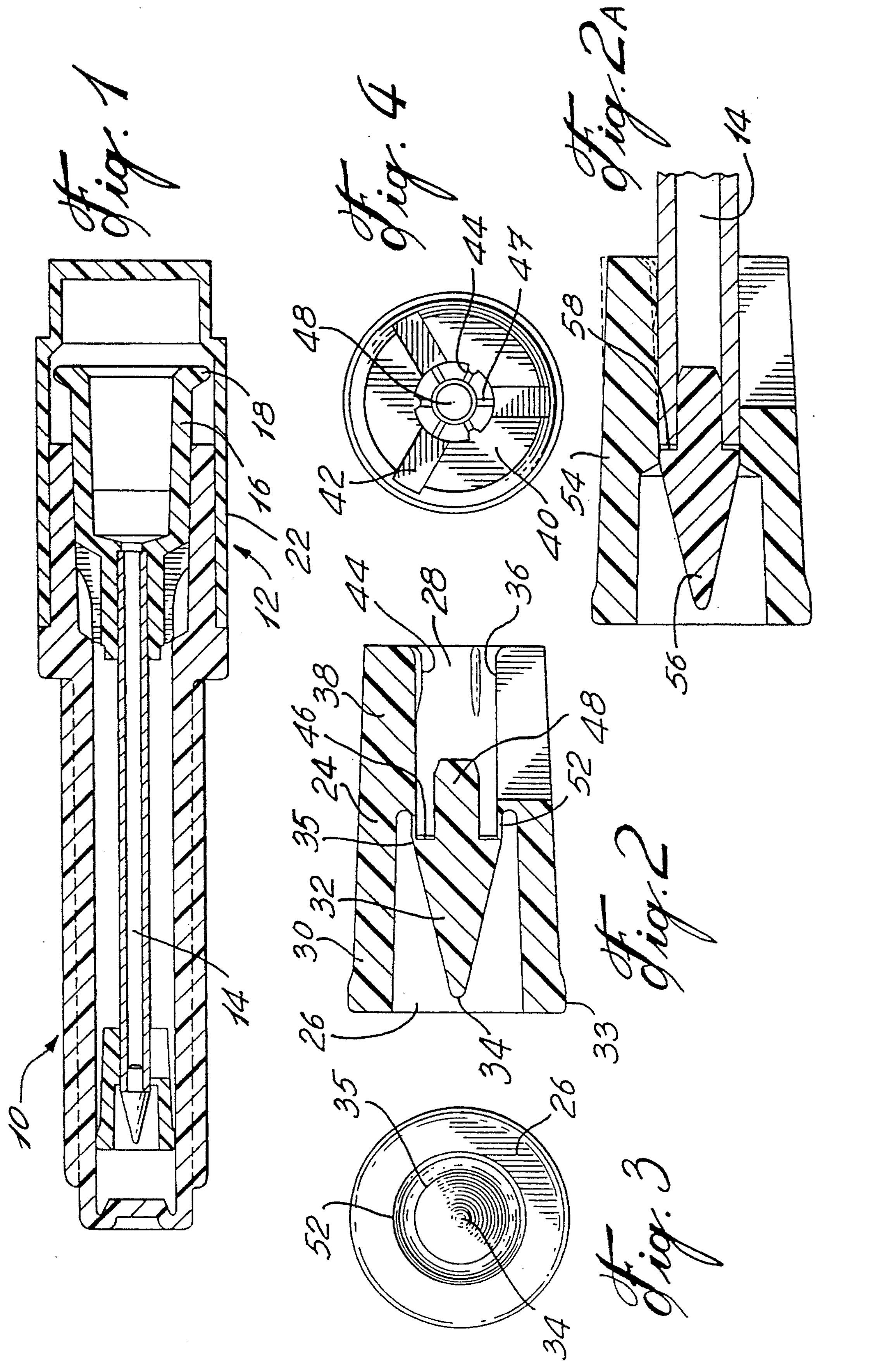
FIG. 1 is a cross-sectional view of the cannula adapter, according to the present invention, mounted on a blunt cannula and packaged in a sterile case ready for use.
FIG. 2 is an enlarged view of the preferred embodiment of the cannula adapter only of FIG. 1.
FIG. 2A is an alternate embodiment similar to FIG. 2.
FIG. 3 is a front view of FIG. 2.
FIG. 4 is a rear view of FIG. 2.

With reference now to FIG. 1, cannula adapter 10 is shown assembled to a blunt cannula device 12 such as an Abbott LifeShield® Blunt Cannula. The blunt cannula includes a steel (or plastic) cannula member 14 and a molded plastic hub 16 securing the cannula. The inlet end of the hub includes a luer connector 18 for attachment to a mating luer connector on a fluid transfer device such as a standard syringe.

The adapter and blunt cannula are assembled and packaged in a two-piece case including bottom member 20 and top member 22. The cannula adapter and blunt cannula assembly are sterilized in a conventional manner.

Referring now to the enlarged FIGS. 2–4, the cannula adapter 10 will now be described. The adapter is preferably a single part, injection molded from a medical grade plastic such as ABS (Acrylonitrile-Butadiene-Styrene). The adapter includes a substantially hollow cylindrical collar 24, having a forward opening end 26 and a rearward opening end 28.

As best seen in FIGS. 2 and 3, the forward opening end 26 is a generally hollow cylinder. The cylindrical wall 30 of the forward end circumferentially surrounds and axially extends forward beyond a piercing element 32. The point or tip 34 of the piercing element is recessed axially from the forward edge of the cylindrical wall 30. The most forward part of the wall is flared 33 (or made thicker) to provide greater surface area for the adapter to abut the elastomer stopper so as to prevent cutting by the collar wall. Also the flared end 33 is used by automated assembly machines to distinguish and directionally orient the forward end of the cannula adapter 10 relative to the cannula 12 for proper assembly.

The piercing element 32 conically increases in diameter from the recessed tip 34 to an outer diameter at 35 that allows for a predetermined clearance of the piercing element 32 through the inside diameter of the forward cylindrical wall 30.

Referring now to FIGS. 2 and 4, the rearward opening end 28 of the adapter is substantially cylindrical and defines a center bore 36. The inside wall 38 of the rearward opening end 28 is divided into a preselected number of radially flexible segments 40 by the longitudinal gaps 42. Three flexible gripping segments 40 are shown for example which are cantilevered from the annular collar 24. A small raised lip 44 is provided on the inner surface of each of the segments 40 so that a cylindrical device, such as the blunt cannula (shown in phantom in FIG. 2A for example), is subjected to an interference fit when inserted into the center bore 36 of the rearward end.

An annular, radially oriented shoulder 46 defines both the rear end of the piercing element 32 and the bottom of the center bore 36. Small radial passageways 47 are provided on the face of the annular shoulder 46 to allow fluid (ie air) to communicate from outside the adapter through the cannula bore to the syringe chamber. It is common practice to initially pressurize the sealed container with air from the syringe chamber. A cylindrical base portion 48 concentrically extends rearward from the shoulder 46. The annular shoulder 46 and the cylindrical base 48 are sized to loosely fit the gauge and bore, respectively, of the blunt cannula.

A circumferential connection 52 connects the cylindrical collar 24 with the piercing element 32. In the preferred embodiment the connection 52 is frangible and includes a radially thin circumferential sleeve molded between the outer diameter 35 of the piercing element 32 and the rear cylindrical wall 38. In an alternative embodiment shown in FIG. 2A, the collar 54 and the piercing element 56 are manufactured separately and are assembled and joined together at the joined mechanical connection 58 by force, friction, adhesive, or any other suitable joining method. For both the integrally molded one piece and separately manufactured and later mechanically connected two piece embodiments, approximately 4 lbs. of axial force is required to separate the piercing element 32 or 56 from the cylindrical collar 24 or 54.

Figures 5, 6, 7, 8:
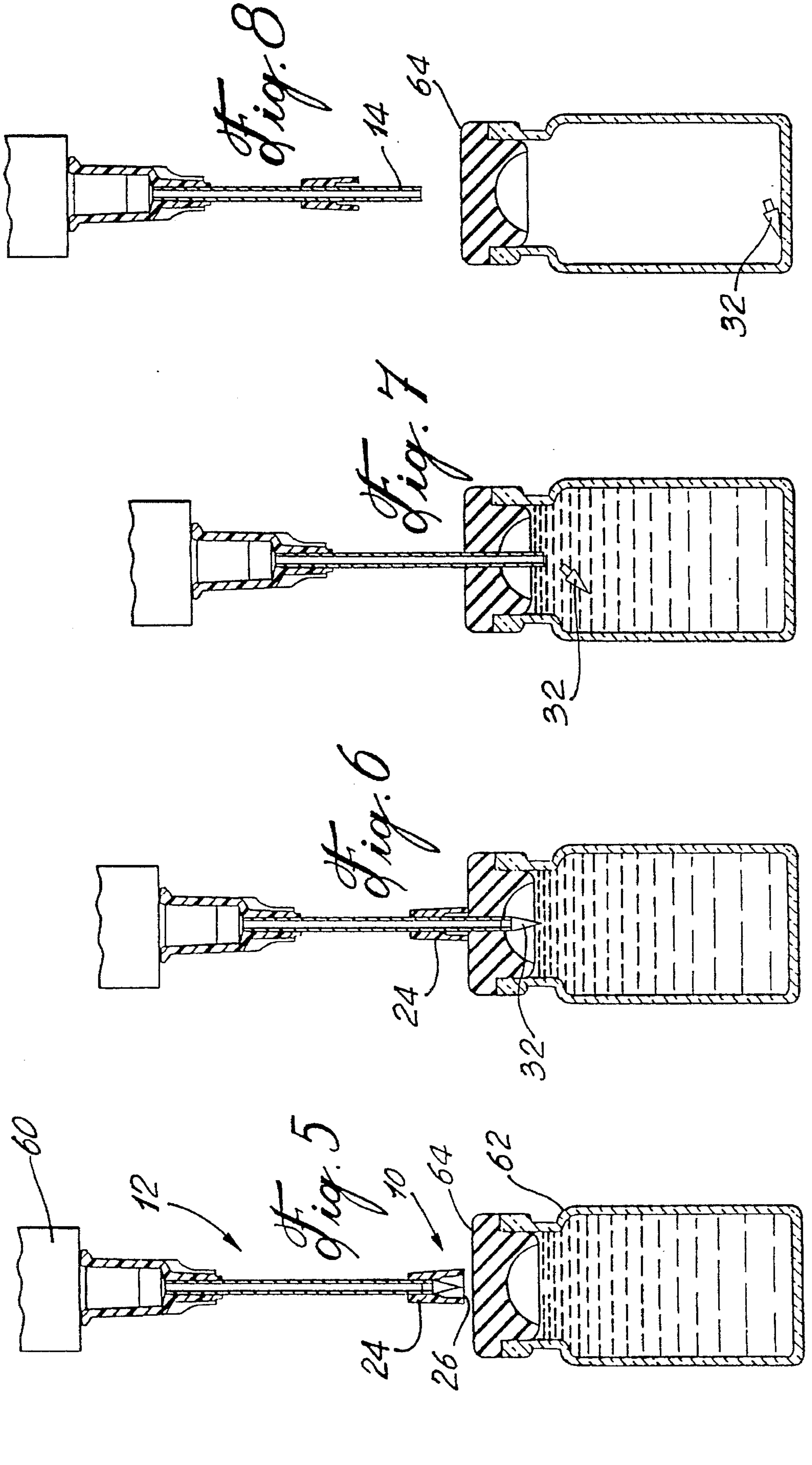
FIG. 5 is a cross-sectional view of the cannula adapter of the present invention prior to use with a blunt cannula connected to a syringe.
FIG. 6 is a cross-sectional view of the cannula adapter of FIG. 5 abutting and piercing an elastomeric stopper.
FIG. 7 is a cross-sectional view of the cannula adapter of FIG. 5 after the piercing element has disengaged from the blunt cannula.
FIG. 8 is a cross-sectional view of the blunt cannula of FIG. 5 after disengaged and withdrawn from the empty vial.

Referring now to FIGS. 1 and 5, the assembled blunt cannula 12 and piercing adapter 10 have been attached to the mating lure connector of a standard syringe 60. The blunt cannula assembly of FIG. 1 is attached to the syringe by removing top cover 22 so as to expose the luer connector 16 which is then attached to a mating connector on the syringe 60. The bottom portion 20 of the packaging can then be removed from the hub 16 to expose the cannula 14 and the adapter 10. At this point in time, if the adapter will not be utilized the adapter 10 can be removed from the blunt cannula 14 merely by gripping the adapter at the collar 24, for example, and pulling the adapter 10 axially off the cannula 14. The syringe now is configured as a bare blunt cannula.

However, if the healthcare provider needs a dose of solution from a medical container such as the stoppered vial 62 in FIG. 6, the syringe plunger is pulled back slightly, as is common practice. This allows air into the syringe chamber for the purpose of pressurizing the vial. With the adapter assembly 10 in place, the syringe and adapter is positioned in abutting contact with the elastomeric stopper 64 so that the forward end 26 of the collar is in contact with the target area of the stopper.

Further axial force of approximately 4 lbs., is applied to the syringe to disconnect the piercing element 32 from the collar 24 at the frangible connection 52. The piercing element 32 now allows the blunt cannula 12 to penetrate through the stopper with approximately 4 lbs. of force. This force is significantly less than the force required to penetrate the stopper with only a blunt cannula.

Referring now to FIG. 7, once the cannula assembly has completely penetrated the stopper, the vial is pressurized by moving the syringe plunger forward. If the stem portion of the piercing element 32 has not yet disengaged from the cannula, the pressurizing fluid will push the stem from the cannula as shown. The solution can then be withdrawn from the vial by the syringe in the normal manner. It is also possible to draw small amounts of fluid into the syringe chamber via the radial passageways 47 on the face of the annular shoulder 46 with the stem still resident in the cannula bore.

Referring now to FIG. 8, when the syringe is filled and the cannula 14 is extracted from the stopper, the piercing element 32 remains inside the vial. The syringe is now configured as a blunt cannula syringe and can be used in conjunction with suitable pre-slit septums such as for example the Abbott LifeShield® Prepierced Reseal.

The present invention advantageously allows a blunt cannula to pierce a stopper with the addition of the piercing element 32 while still preventing accidental stick from the piercing element 32 due to the recessed position and shielding wall 30. Since the blunt cannula comes packaged with the piercing adapter 10 already attached, time is saved by the user because the adapter does not have to be unpackaged and attached by the user. Also, risk of contamination to the cannula is reduced because the adapter is already attached. Furthermore, the piercing adapter 10 can be readily removed without compromising the sterility of the blunt cannula because only the collar 24 of the adapter is touched.

Another advantage of the present invention is that the adapter is economical to manufacture, especially in the preferred integral embodiment since the adapter can be molded in one piece and is easily machine assembled to the blunt needle prior to packaging and sterilization. Also, since the adapter is packaged with the blunt cannula, no additional disposal of packaging materials is required.

From the foregoing, it will be observed that numerous modifications and variations can be affected without departing from the true spirit and scope of the novel concept of the present invention. It is to be understood that no limitation with respect to the specific embodiment is intended or should be inferred. Disclosures intended to be covered by the appended claims and all such modifications as fall within the scope of the claims.

We claim

1. A piercing member constructed and arranged for use with an associated blunt end of a hollow bore cannula to pierce an elastomeric closure, the piercing member comprising:

an annular collar having a generally cylindrical outside surface, a hollow rearward extending portion having a first inside diameter wall surface constructed and arranged for an interference fit around the blunt end of the cannula, and a hollow forward extending portion having a second inside diameter wall surface having an end constructed and arranged to abut the closure, the diameter of the first inside wall surface being less than the diameter of the second inside wall surface;

a detachable piercing element concentrically positioned within the second inside wall surface of the annular collar and having a conical portion oriented axially forward within the forward portion of the collar and abase portion within the rearward portion of the collar; and a frangible connection for detachably connecting the piercing element to the first inside wall surface.

2. The piercing member of claim 1 wherein the annular collar is initially a separate part and the detachable piercing element is initially a separate part and the frangible connection is a mechanically joined connection of the two separate parts.

3. The piercing member of claim 1 wherein the frangible connection is a thin annular sleeve axially extending between the detachable piercing element and the inside wall surface of the rearward portion of the collar.

4. The piercing member of claim 3 wherein the base portion is a cylindrical stem constructed and arranged to fit within the hollow bore of the cannula.

5. The piercing member of claim 4 wherein the piercing element includes a radial shoulder at the juncture of the conical portion and the base portion.

6. The piercing member of claim 5 wherein the radial shoulder includes radial passageways for longitudinal fluid flow.

7. The piercing member of claim 5 wherein the conical portion of the piercing element increases in diameter from a conical tip point to the radial shoulder.

8. The piercing member of claim 7 wherein the conical portion has an outer diameter which is greater than the outer diameter of the blunt end of the cannula.

9. A cannula assembly constructed and arranged to pierce a stopper, comprising:

a cannula hub having a first and second end, the first end constructed and arranged for fluid flow connection;

a cannula extending from the second end of the hub and terminating in a blunt end;

a flow passageway through the cannula for fluid communication between the first end of the hub and the blunt end of the cannula;

a disposable piercing member including:

an annular collar having a rearward end constructed and arranged for an interference fit around the blunt end of the cannula and a forward extending end constructed and arranged for abutment with the stopper;

a piercing member concentrically positioned within the annular collar and having a pointed tip orientated forward within the forward end of the collar and a base portion within the rearward end of the collar; and a frangible connection circumferentially connecting the annular collar and the piercing member.

10. The cannula assembly according to claim 9 wherein the frangible connection is a thin annular sleeve axially extending between the piercing member and the annular collar.

11. The cannula assembly according to claim 9 wherein the frangible connection is a mechanically joined connection.

* * * * *